US006548300B1

(12) United States Patent
Sandal et al.

(10) Patent No.: US 6,548,300 B1
(45) Date of Patent: Apr. 15, 2003

(54) ONE STEP METHOD FOR MICRO-PRODUCTION OF TEA LEAVES

(75) Inventors: Indra Sandal, Palampur (IN); Amita Bhattacharya, Palampur (IN); Madhu Sharma, Palampur (IN); Paramvir Singh Ahuja, Palampur (IN)

(73) Assignee: Council of Scientific & Industrial Research, New Delhi (IN)

( * ) Notice: Subject to any disclaimer, the term of this patent is extended or adjusted under 35 U.S.C. 154(b) by 43 days.

(21) Appl. No.: 09/811,777

(22) Filed: Mar. 20, 2001

(51) Int. Cl.[7] .............................. C12N 5/00; C12N 5/02; A01H 11/00; A01H 9/00

(52) U.S. Cl. ........................ 435/420; 800/295

(58) Field of Search .......................................... 435/420

Primary Examiner—Bruce R. Campbell
Assistant Examiner—Susan B. McCormick
(74) Attorney, Agent, or Firm—Foley & Lardner

(57) ABSTRACT

The invention provides a one step method for micropropagation of tea plants from leaf explants via callus phase, wherein the explants are maintained in basal Murashige and Skoog medium (Murashige T. and Skoog F. A revised medium for rapid growth and bioassays with tobacco tissue cultures. Physiol. Plant. 15: 473–497; 1962) supplemented with vitamins like thiamine-HCl (0.05 to 2.0 mg/l), pyridoxine-HCl (0.25 to 1.5 mg/l) and nicotinic acid (0.25 to 1.5 mg/l) together with glycine (1.0 to 3.0 mg/l) and either 2.5, 5.0 or 7.5 mg/l 2,4-Dichlorophenoxy acetic acid for a period of 14–16 weeks, from the stage of induction of callus to rhizogenesis and shoot formation.

18 Claims, 1 Drawing Sheet

ONE STEP METHOD FOR MICRO-PRODUCTION OF TEA LEAVES

FIELD

The present invention relates to a novel one step method for micro-shoot production from tea leaves.

BACKGROUND

Tea is a popular caffeine containing beverage with anti-cancerous properties (Jankun, J., Selman, S. H., Swiercz, R. Why drinking green tea could prevent cancer. Nature 5:561; 1997). Although the genus Camellia has many species only *C. sinensis* (L.) O. Kuntze or tea and its different cultivars like the Chinary, Assamica and Cambod are commercially important (Barua, D. N. The tea plant of commerce In: Barua, D. N., ed. Science and practice in tea culture, Tea Research Association Calcutta; 53–68; 1989).

Tea cultivation is not only an important employment generator but is also a major foreign exchange earner in all the tea growing areas of the world (Wilson, K. C. Botany and Plant Improvement In: Wilson R. C., ed. Coffea, Cocoa and Tea. CABI Publishing, Wallingford, UK: 167–173; 1999). However, the total production of tea is not sufficient enough to meet the demands of the domestic and the world markets (Kabra, G. D. Tea statistics for 1999 In: Tea time, Vol VIII, No. 3 Sep–Nov 99, 30–31; 1999). The yield and quality of tea is further reduced by different biotic (fungi, pests and viruses) and abiotic (frost, hail, chilling, drought, nutritional deficiencies etc.) stresses (Wilson, K. C. Botany and Plant Improvement In: Wilson R. C., ed. Coffea, Cocoa and Tea. CABI Publishing, Wallingford, UK: 167–173; 1999).

Tea actually being a woody tree species has a long life cycle coupled with a high degree of self incompatibility and inbreeding depression (Barua, D. N. The tea plant of commerce In: Barua, D. N., ed. Science and practice in tea culture, Tea Research Association Calcutta; 53–68; 1989) that generally limit the production of high yielding but superior and stress resistant tea plants through conventional breeding. Therefore, application of biotechnological means would be an effective and alternative approach. However, an efficient as well as reproducible regeneration protocol is the most important pre-requisite for any biotechnological application.

The most severe problem in tea is the blister blight disease because it afflicts the young leaves and shoots that are used for making tea. As a result 50% loss in tea yield is incurred. Therefore, resistance to blister blight is urgently required to compensate for this loss. Some clones have been identified which are high yielding as well as of high quality but these are, susceptible to blister blight disease and hence require biotechnological improvements through homogenous tissues like leaf explants because heterogeneous tissues like cotyledon explants would result in genetic segregation and loss of the desirable characters of high yield and good quality. Therefore, the existing protocols involving heterogeneous tissues like cotyledon explants is of no use with respect to the above objective and also where the true to type character of an elite plant needs to be maintained. Therefore, there is an urgent need to develop methods for micropropagation using homogenous tissues. Regeneration from leaf explants are maximally preferred because:

(i) leaf explants are homogenous
(ii) regeneration from leaf explants would always result in the development of plants true to type to the original selected elite
(iii) leaves have chloroplast DNA that have extremely high copy number and thus, the level of expression can be amplified by several folds if leaves are used while doing any genetic manipulations like the development of transgenics or somatic hybrids.
(iv) leaves offer larger surface area for application of any genetic manipulation techniques.
(v) leaves are the major commercial source of made tea sold in the market.
(vi) leaves provide an abundant supply of starting material.
(vii) using leaves as explants will not hamper the general well being and growth of the plant.

Biotechnological crop improvement either through somatic hybridization or through transgenic technology generally requires regeneration via callus phase provided there is no creation of somaclonal variants during the regeneration process. Since tea has a long life span, chances of chromosomal variability in the callus phase is low as compared to that of fast growing herbaceous plants. Therefore, the applicants report an efficient one step method for the micropropagation of tea plants using leaf explants via callus phase. The regeneration ability of the woody plants is difficult and more so if either leaf explants are used or if the plants are very old trees of about 50 years or more.

Leaf explants have been used in other ornamental species of Camellia i. e. *C. japonica* and *C. reticulata* (Sanjose, M. C. and Vieitez, A. M. Adventitious shoot regeneration from in vitro leaves of adult *Camnellia reticlilata*. J.Hort.Sci. 67: 677–683; 1992; Sanjose, M. C. and Vieitez, A. M. Regeneration of Camellia plantlets from leaf explant cultures by embryogenesis and caulogenesis.Sci.Horti.54: 303–315; 1993; Pedroso, M. C. and Pais, M. S. Direct embryo formation in leaves of *C. japonica* L. Plant Cell Rep.12: 639–643; 1993) for generating plants via somatic embryogenesis or adventitious shoot bud formation via callus phase but either the conversion frequency was low (4–6%) or rooting was poor. Moreover, these are all ornamental species. There is no report of plant regeneration from leaf explants for adventitious shoot bud formation through callus in *C. sinensis* i.e. the commercial Camellia or tea. Also there is no report till date on one step method of shoot regeneration from leaf explants in either tea or any of the other ornamental species.

Attempts were first made in 1984 by Nakamura, (Nakamura Y. Effective methods of in vitro propagation of tea plant. Proc. Internat. Symp. On Recent Development in Tea Production, Taiwan Republic of China. 1984: 63–74pp) for developing regeneration protocol from leaf explants wherein callus was obtained on Nitsch and Nitsch's medium (Nitsch, J. P. and Nitsch C., Haploid plants from pollen grains. Sci. (Washington), 163: 85–87; 1969) and Gamborg's medium (Gamborg, O. L., Miller, R. A. and Ojima, K. Nutrient requirements of suspension cultures of soyabean root cells. Experimental Cell Research 50: 151–58; 1968) supplemented with an auxin 2,4-Dichlorophenoxy acetic acid. The drawback of the method is that he failed to obtain morphogenesis or adventitious shoot bud formation despite using different media in the different steps of morphogenesis.

Again in 1985, Nakamura (Nakamura, Y. Effects of origin of explants on differentiation of root and its varietal difference in tissue culture of tea plants. Shizuoka Tea Experimental Station 62: 1–8; 1985) and Palni, Sood, Chand, Sharma, Rao and Jain (Palni, L. M. S., Sood, A., Chand, G., Sharma, M., Rao, D. V., Jain, N. K. Tissue culture studies in tea. Proc. International Sym. On Tea Science, Shizuoka, Japan. 395–399; 1991) attempted to regenerate plants from leaf explants through callus wherein rhizogenesis or root formation was obtained from the leaf callus however, the drawback was that such rhizogenic calli failed to produce shoots and two different media were used. Thereafter, there was no report on plant regeneration from leaf explants until in 1996 wherein Kato (Kato, M. Somatic embryogenesis from immature leaves of in vitro grown tea shoots. Plant Cell Rep.15: 920–926; 1996) obtained a few plants from somatic embryos derived from leaf explants of in vitro grown plants on Murashige and Skoog medium (Murashige T. and Skoog F. A revised medium for rapid growth and bioassays with tobacco tissue cultures. Physiol. Plant. 15: 473–497; 1962) supplemented with 0.5 mg/l 2,4-Dichlorophenoxy acetic acid in liquid and 5 mg/l 2,4-Dichlorophenoxy acetic acid in 0.8% agar solidified medium.

The major drawbacks of Kato's protocols are enumerated as follows:

(i) The percent of explant response with respect to induction of somatic embryo is very low (6%).

(ii) The donor plants are seedlings leading to genetic variations in the progenies.

(iii) The frequency of somatic embryo conversion into plants is very poor i. e. 7.1%.

(iv) The embryos induced were confined to specific regions of the leaf and not from all over the leaf surface rendering them unsuitable for transgenic studies.

(v) Does not involve a system for culturing leaf explants from mature selected bushes with elite characters rather it involves development of embryogenic calli from leaf explants of seedlings.

(vi) Seedlings represent heterogenous population whereas, explants collected from selected mature trees represent elite characters because they are propagated through clonal or vegetative means.

(vii) Different media were used for different steps like embryo induction, secondary embryogenesis and embryo germination.

OBJECTS OF THE INVENTION

The main objective of the present invention is to develop healthy shoots from leaf explants of tea in a single step.

Another object of the present invention is to introduce foreign genes of interest into leaf explants and develop large number of genetically modified plants both directly through biolistic gun or through Agrobacterium.

Still another object of the present invention is to develop an efficient micropropagation method that is cost effective single step method using a single plant growth hormone.

Still another object of the present invention is to develop a cost and labour effective efficient method for the micropropagation of tea from leaf explants by using only 25 ml medium in plastic petridishes (autoclavable) and by avoiding subculturing.

Still another object of the present invention is to develop an efficient method for micropropagaiton for leaf derived protoplasts and somatic hybridization without the requirement for further subculturing, once the hybrid callus is formed.

Yet another object of the present invention is to introduce genes of interest into protoplasts and study their expression.

Yet another object of the present invention to facilitate the uptake of virus particles in viral diagnostic programmes.

SUMMARY OF THE INVENTION

Accordingly, the invention provides a novel method to develop healthy shoots from leaf explants of tea in a single step:

DETAILED DESCRIPTION OF THE INVENTION

Accordingly, the invention provides a novel and efficient, simple, cost and labour effective method for tea micropropagation from leaf explants wherein, shoots can be developed from leaves of any cultivar (i.e. Chinary, Cambod or Assamica) of commercial Camellia or tea. The leaves that are $2^{nd}$ and $3^{rd}$ from the shoot tips are placed on 25 ml standard basal Murashige and Skoog medium containing 2,4-Dichlorophenoxy acetic acid (5.0–10.0 mg/l) but preferably 5.0 mg/l 2,4-D in 9.0 cm plastic petridishes (autoclavable) without any subculturing to fresh medium of any kind. Callusing is observed all over the surface of the leaf explants after a period of atleast 2–4 weeks but preferably after 2 weeks. Rhizogenesis or root formation is observed on the same medium in the same petridish after a period of atleast 4–6 weeks but preferably after 4 weeks. Lastly shoot formation is also observed on the same medium in the same petridish after 4–6 weeks but preferably after 4 weeks. The novelty of the method is that it (a) does not require any subsequent steps, (b) requires only one plant growth regulator 2,4-Dichlorophenoxy acetic acid (5.0–10.0 mg/l), (c) requires no subculturing, (d) the overall process requires only 25 ml medium at the beginning of the process (e) all the steps of morphogenesis (rhizogenesis and shoot formation) can be observed on the same medium (as it gradually gets depleted) thereby, making the method both cost and labour effective.

Accordingly the present invention provides a novel one step method for micro-shoot production from tea leaf explants comprising only a single step method comprising of about 10–16 weeks wherein (a) leaf explants of in vitro raised plants of any cultivar (Chianry, Assamica, Cambod) are placed on 25 ml of agar solidified (0.8–1.0%) standard basal Murashige and Skoog medium (Murashige T. and Skoog F. A revised medium for rapid growth and bioassays with tobacco tissue cultures. Physiol. Plant. 15: 473–497; 1962) supplemented with vitamins like thiamine-HCl (0.05 to 2.0 mg/l), pyridoxine-HCl (0.25 to 1.5 mg/l) and nicotinic acid (0.25 to 1.5 mg/l) together with glycine (1.0 to 3.0 mg/l), 2,4-Dichlorophenoxy acetic acid (5.0–10.0 mg/l) contained in 9.0 cm autoclavable plastic petridishes (b) callus development is observed after 2–4 weeks but preferably after 2 weeks on the same medium (b) rhizogenesis or root formation is observed on the leaf calli lying on the same but partially depleted medium after 4–6 weeks (c) finally shoot formation is also observed on the rhizogenic calli lying on the same but almost dried and depleted medium after 4–6 weeks (d) shoots thus formed are transferred for multiplication to a multiplication medium consisting of liquid medium-supplemented with 5 μm Thidiazuron (Sandal I., Bhattacharya A. and Ahuja P. S. 2001 An efficient liquid culture system for tea shoot proliferation. Plant Cell Tiss. Organ Culture 00. 1–6) (e) and for rooting, the cut ends of at least 3.0 cm long shoots are treated with Indole-3-butyric acid for a period of 20–30 minutes and transferred to sterile sand soil mix (1:1) covered with jars for at least (60–75 days) days before transferring them to open plastic pots (Sandal I., Bhattacharya A. and Ahuja P. S. 2001 An efficient liquid culture system for tea shoot proliferation. Plant Cell Tiss. Organ Culture 00. 1–6).

In an embodiment of the present invention fresh completely folded, half opened or fully expanded leaves from selected plants of three cultivars (Chinary, Assamica and Cambod) growing in the fields were used as explants. The leaves were cleaned in the solution containing Bavistin (0.1%) and streptomycin (0.05%), washed in Tween 20 and surface sterilized in 0.01% (w/v) mercuric chloride solution containing a drop of liquid detergent followed by thorough washings in sterile distilled water. The surface sterilized explants were then cultured as in the above mentioned method.

In yet another embodiment of the present invention leaf explants of either in vitro or ex vitro raised selected plants of hybrid cultivars of the Chinary, assamica and Cambod types were used as in above.

(i) Completely folded, half opened or fully expanded leaf explants of in vitro raised cultures of hybrids of any cultivar were placed on standard basal Murashige and Skoog medium (Murashige T. and Skoog F. A revised medium for rapid growth and bioassays with tobacco tissue cultures. Physiol. Plant. 15: 473–497; 1962) supplemented with vitamins like thiamine-HCl (0.05 to 2.0 mg/l), pyridoxine-HCl (0.25 to 1.5 mg/l) and nicotinic acid (0.25 to 1.5 mg/l) together with glycine (1.0 to 3.0 mg/l) and most importantly 2,4-Dichlorophenoxy acetic acid (5.0–10.0 mg/l) contained in 9.0 cm autoclavable plastic petridishes were incubated for 10–16 weeks in the same dishes at 25±2° C. with cool fluorescent light (52 $\mu molm^{-2}s^{-1}$) for callus induction followed by rhizogenesis and finally adventitious shoot bud formation on same medium.

(ii) The shoot buds obtained from above step after 10–16 weeks were excised and were multiplied in static 20 ml liquid medium containing 3% sucrose and 5 $\mu M$ Thidiazuron (Sandal I., Bhattacharya A. and Ahuja P. S. 2001 An efficient liquid culture system for tea shoot proliferation. Plant Cell Tiss. Organ Culture 00. 1–6).

(iii) The micro-shoots were rooted by treating the cut ends with 5 mg/l IBA and planting in sterile sand: soil (1:1) mix in pots covered with inverted jars under culture lab conditions for 8 weeks and then transferring rooted shoots to plastic pots under ambient temperatures (Sandal I., Bhattacharya A. and Ahuja P. S. 2001 An efficient liquid culture system for tea shoot proliferation. Plant Cell Tiss. Organ Culture 00. 1—6).

Presence of 2,4-Dichlorophenoxy acetic acid at high concentrations in the medium is known to induce active cell division and undifferentiated growth resulting in callus formation in plant tissues. Callus formation at specific concentrations of 2,4-Dichlorophenoxy acetic acid in the medium is perhaps due to the uptake and increase in the intracellular 2,4-D levels. However when the calli are left for an extended period of time (i.e. 10–16 weeks) on the medium there is a progressive dilution of 2,4-Dichlorophenoxy acetic acid both in the medium and in the intracellular levels as a result of continued callus growth. This reduction in the level of 2,4-Dichlorophenoxy acetic acid both in the medium and in the intracellular levels coupled with partial depletion of nutrients in the medium probably results in stressful condition and hence in morphogenesis or a large number of root formation. Further decrease in the level of 2,4-Dichlorophenoxy acetic acid and the nutrients in the medium due to drying and depletion of the medium probably leads to shoot formation and simultaneous drying of calli. The critical threshold level of 2,4-Dichlorophenoxy acetic acid at each step of morphogenesis is probably achieved by progressive sequestering of 2,4-Dichlorophenoxy acetic acid with the passage of time either in the form of callus growth or by root growth and gradual depletion of the medium. Initiation of shoot buds occur when sufficient root growth coupled with continued callus growth on 2,4-D depleted medium occurs. Thus, an intracellular threshold value of 2,4-D at each step of morphogenesis, its sequestration and stressful condition due to medium depletion are probably essential for directing the leaf tissue towards a programme of regeneration through dedifferentiation.

The novel features of the method that obviates the drawbacks detailed above are as follows:

(i) The method involves a single step for tea shoot production from leaf explants.

(ii) The percent response (almost 100%) of leaf explant is high.

(iii) Leaf explants from mature selected tea plants (both ex vitro and in vitro) respond efficiently in this method.

(iv) The method is quite effective for clonal propagation of selected/elite clones.

(v) The method can also be used for leaf explants derived from seedlings.

(vi) The method is effective for both folded and unfolded leaves.

(vii) The method is effective for leaf explants of any cultivar (Chinary, Assamica and Cambod)

(viii) The method involves callus formation which develops from all over the surface and is not localised to specific regions of the leaf surface as in case of somatic embryos.

(ix) This method enables the production of more than 10–15% adventitious shoot formation that can be later rooted for its development into healthy plants (x) This is the first report on one step method for the development of highest frequency of tea shoots callus formation on leaf explants. This is in contrast to all the previous reports that have failed to achieve plants from leaf explants through adventitious buds even after applying many steps.

(xi) This method offers a potential for higher frequency of transgenic tea plant production through genetic transformation as compared to the protocol suggested by Kato (1996). This is because the protocol offers the potential for single cells that are genetically transformed to have much higher chances of multiplying and making the transformant successful as compared to the low frequency of genetically transformed somatic embryos that are due to the region specific induction.

Figure 1:
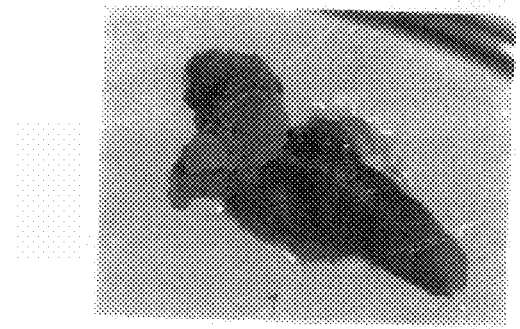
FIG. 1 represents induction and proliferation of callus on the leaf explants
Figure 2:
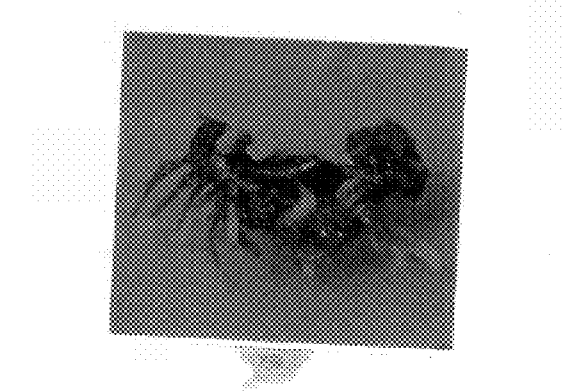
FIG. 2 represents rhizogenesis or root formation from all over the callus derived from the leaf explants. (Rhizogenesis represents the turning point where the path of undifferentiated growth is shifted to a path of morphogenesis).
Figure 3:
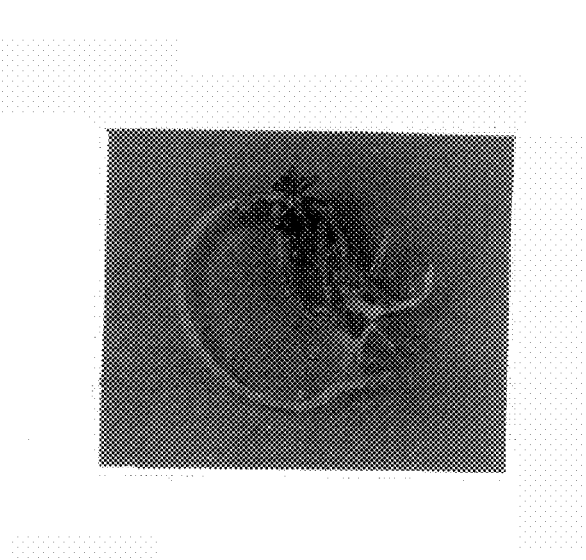
FIG. 3 represents adventitious shoot bud formation from the roots that were formed on the leaf callus
Figure 4:
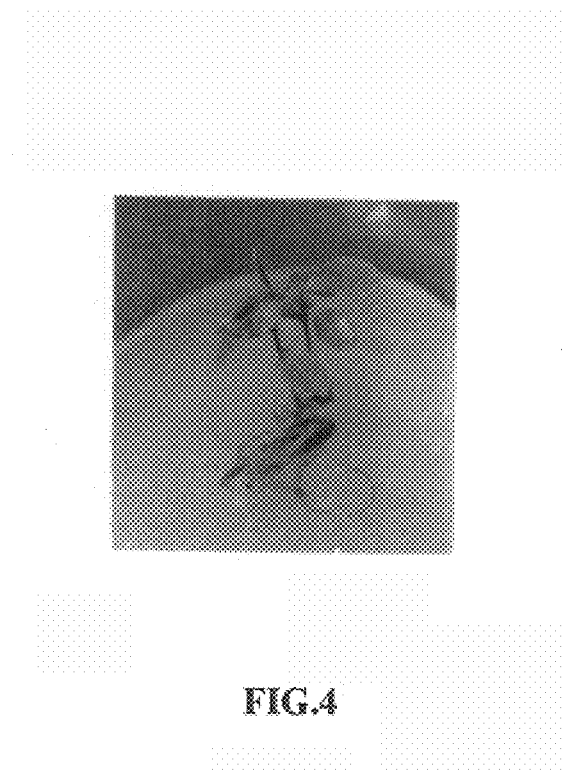
FIG. 4 represents the rooted microshoots that were developed indirectly from leaf explants.

The following examples are given by way of illustration and therefore should not be construed to limit the scope of the present invention.

EXAMPLE-1

Any leaf ranging from completely folded, half opened or fully expanded leaf explants of in vitro raised plants of the important cultivars (Chinary, Assamica and Cambod) were the responsive explants when they were placed on (0.8–1%) agar solidified basal Murashige and Skoog medium (Murashige T. and Skoog F. A revised medium for rapid growth and bioassays with tobacco tissue cultures. Physiol. Plant. 15: 473–497; 1962) supplemented with vitamins like thiamine-HCl (0.05 to 2.0 mg/l), pyridoxine-HCl (0.25 to 1.5 mg/l) and nicotinic acid (0.25 to 1.5 mg/l) together with glycine (1.0 to 3.0 mg/l) and 2.5 to 10.0 mg/l 2,4-Dichlorophenoxy acetic acid (pH 5.6±0.2) for 10 to 16 weeks at a temperature of 25±2° C. and a photoperiod of 16 h under cool fluorescent light of 52 $\mu$mol m$^{-2}$s$^{-1}$. Callus is developed 1–2 weeks after culture intiation on basal Murashige and Skoog medium (Murashige T. and Skoog F. A revised medium for rapid growth and bioassays with tobacco tissue cultures. Physiol. Plant. 15: 473–497; 1962) supplemented with vitamins like thiamine-HCl. (0.05 to 2.0 mg/l), pyridoxine-HCl (0.25 to 1.5 mg/l) and nicotinic acid (0.25 to 1.5 mg/l) together with glycine (1.0 to 3.0 mg/l) and 2,4-Dichlorophenoxy acetic acid (5.0–10.0 mg/l) followed by rhizogenesis after 4–6 weeks and shoot formation after further 4–6 weeks on the same but dried and depleted medium. Shoots thus formed are transferred to a multiplication medium consisting of liquid medium supplemented with 5 $\mu$m Thidaizuron (Sandal I., Bhattacharya A. and Ahuja P. S. 2001 An efficient liquid culture system for tea shoot proliferation. Plant Cell Tiss. Organ Culture 00. 1–6), and for rooting the cut ends of at least 3.0 cm long shoots are treated with Indole-3-butyric acid for a period of 20–30 minutes and transferred to sterile sand soil mix (1:1) covered with jars for at least (60–75 days) days before transferring them to open plastic pots.

EXAMPLE-2

Any leaf ranging from completely folded, half opened or fully expanded leaf explants (2$^{nd}$ and 3$^{rd}$ leaves from the shoot tip) of 50 years old selected plants of important cultivars (Chinary, Assamica and Cambod) from the Institute of Himalayan Bioresource Technology's Experimental farm, Banuri, Palampur (36°N and 78.18°E and 1290 m above sea level) were used as explants. The leaves were cleaned carefully with a sable hair brush and liquid detergent, washed in Tween20 containing Bavistin (0.1%) and streptomycin (0.05%) and surface sterilized in 0.01% mercuric chloride solution containing a drop of liquid detergent followed by a thorough rinse in distilled water. The sterilized explants were cultured similarly as per details given in the above mentioned protocol.

EXAMPLE-3

Any leaf ranging from completely folded, half opened or fully expanded leaf explants of in vitro raised plants of other hybrid cultivars were placed on (0.8–1%) agar solidified basal Murashige and Skoog medium (Murashige T. and Skoog F. A revised medium for rapid growth and bioassays with tobacco tissue cultures. Physiol. Plant. 15: 473–497; 1962) supplemented with vitamins like thiamine-HCl (0.05 to 2.0 mg/l), pyridoxine-HCl (0.25 to 1.5 mg/l) and nicotinic acid (0.25 to 1.5 mg/l) together with glycine (1.0 to 3.0 mg/l), supplemented with 3% sucrose and 2.5 to 10.0 mg/l 2,4-D (pH 5.6 +0.2) for 10–16 weeks at a temperature of 25±2° C. and a photoperiod of 16 under cool fluorescent light of 52 $\mu$mol m$^{-2}$s$^{-1}$ for callus development after 1–2 weeks followed by rhizogenesis after 4–6 weeks and shoot formation after further 4–6 on the same medium. Shoots thus formed were then transferred for multiplication to a multiplication medium consisting of liquid medium supplemented with 5 $\mu$m Thidaizuron (Sandal I., Bhattacharya A. and Ahuja P. S. 2001 An efficient liquid culture system for tea shoot proliferation. Plant Cell Tiss. Organ Culture 00. 1–6), and for rooting by treating the cut ends of at least 3.0 cm long shoots with Indole-3-butyric acid for a period of 20–30 minutes and transferring to sterile sand soil mix (1:1) covered with jars for at least (60–75 days) days before transferring them to open plastic pots (Sandal I., Bhattacharya A. and Ahuja P. S. 2001 An efficient liquid culture system for tea shoot proliferation. Plant Cell Tiss. Organ Culture 00. 1–6).

The main advantages of the present invention are:

(1) Healthy plants can be regenerated from truly homogenous tissue like the leaf explants.

(2) The present invention can be used to generate blister blight resistant plants.

(3) The method can also be used for protoplast culture and somatic hybridization.

(4) The method can be applied for chloroplast transformation through direct delivery of genes.

(5) The method is best for developing high frequency transgenics as rapid multiplication of single cell transformants can occur during rapid proliferation of the callus cells as compared to the direct regeneration from leaf tissues without intervening callus.

(6) Frequency of transformants through this method will be much higher than existing protocols as the development of callus is from all over the leaf surface as compared to the region specific induction of somatic embryos in previous reports.

(7) The present invention can be used for developing methods for the introduction of genes of interest into protoplasts and for the study of their expression.

(8) The present invention can be used to facilitate the uptake of virus particles.

(9) The present invention can be used to produce plants expressing maternally inherited traits like cytoplasmic male sterility, tolerance to herbicides like atrazine.

(10) The use of only 25 ml medium in autoclavable plastic petri-dish as compared to the use of 50–100 ml medium in the pre-existing methods makes it a cost effective process.

(11) The present method is cost effective as no subculture is required for the entire process and only 25 ml medium is required.

(12) the present invention is also labor effective as there is no need of subculturing.

What is claimed is:

1. A method for micropropagation of tea plants, comprising culturing tea leaf explants on a single media plate comprising auxin, vitamins, and glycine, whereby callus induction, root rhizogenesis, and shoot formation occur on a single media plate.

2. The method of claim 1, wherein said explants are selected from tea cultivars Chinary, Assamica, and Cambod.

3. The method of claim 1, wherein said explants are excised from the second and third leaves from the shoot tip.

4. The method of claim 1, wherein said explants are cultured on said media plate for a period of 10–16 weeks.

5. The method of claim 1, wherein said auxin is selected from the group consisting of indole-3-acetic acid, naphthaleneacetic acid, and 2,4-dichlorophenoxyacetic acid.

6. The method of claim 5, wherein said auxin is 2,4-dichlorophenoxyacetic acid.

7. The method of claim 6, wherein the concentration range of 2,4-dichlorophenoxyacetic acid is 5.0–10.0 mg/l.

8. The method of claimed 7, wherein said concentration is 5.0 mg/l.

9. The method of claim 1, wherein said vitamins are selected from the group consisting of thiamine-HCl, pyridoxine-HCl, and nicotinic acid.

10. The method of claim 9, wherein the concentration range of thiamine-HCl is 0.05–2.0 mg/l.

11. The method of claim 9, wherein the concentration range of pyridoxine-HCl is 0.25–1.5 mg/l.

12. The method of claim 9, wherein the concentration range of nicotinic acid is 0.25–1.5 mg/l.

13. The method of claim 1, wherein the concentration range of glycine is 1.0 to 3.0 mg/l.

14. The method of claim 1, wherein the pH range of said media is 5.6 to 5.9.

15. The method of claim 14, wherein said pH is 5.6.

16. The method of claim 1, wherein said explants are grown under cool fluorescent light.

17. The method of claim 16, wherein the intensity of said light is 52 $\mu Em^{-2}s^{-1}$.

18. The method of claim 16, wherein the photoperiod of said light is 16 hours.

* * * * *